United States Patent

Beller et al.

Patent Number: 5,675,034
Date of Patent: Oct. 7, 1997

[54] PROCESS FOR PREPARING 2-(P-FLUOROPHENYL)-2 METHYL-PROPIONIC ACID AND 3-(P-FLUOROPHENYL)-2-METHYLPROPIONIC ACID DERIVATIVES

[75] Inventors: Matthias Beller, Niedernhausen; Hartmut Fischer, Hofheim; Heinz Strutz, Usingen, all of Germany

[73] Assignee: Hoechst Aktiengesellschaft, Frankfurt, Germany

[21] Appl. No.: 581,757

[22] Filed: Jan. 2, 1996

Related U.S. Application Data

[63] Continuation of Ser. No. 324,744, Oct. 18, 1994, abandoned.

[30] Foreign Application Priority Data

Oct. 20, 1993 [DE] Germany ............ 43 35 748.2

[51] Int. Cl.$^6$ .................................................. C07C 69/76
[52] U.S. Cl. ..................... 560/105; 562/496; 564/182
[58] Field of Search ............... 560/105; 562/496; 564/182

[56] References Cited

U.S. PATENT DOCUMENTS

| | | | |
|---|---|---|---|
| 3,654,349 | 4/1972 | Shen et al. | 260/515 M |
| 3,766,259 | 10/1973 | Sletzinger et al. | 260/515 A |
| 5,274,171 | 12/1993 | Chalk et al. | 560/104 |
| 5,300,675 | 4/1994 | Elango | 560/55 |
| 5,360,924 | 11/1994 | Beller et al. | 560/55 |

FOREIGN PATENT DOCUMENTS

| | | |
|---|---|---|
| 0 508 586 | 10/1992 | European Pat. Off. |
| 0 553 668 | 8/1993 | European Pat. Off. |

OTHER PUBLICATIONS

March, "Advanced Organic Chemistry", $3_{rd}$ ed., John Wiley & Sons, New York (1985), pp. 642.
Kikukawa et al., *Tetrahedron*, 37, pp. 31–36 (1981).

*Primary Examiner*—Samuel Barts
*Attorney, Agent, or Firm*—Connolly & Hutz

[57] ABSTRACT

Process for preparing 3-(p-fluorophenyl)-2-methylpropionic acid and derivatives thereof of the formula (I),

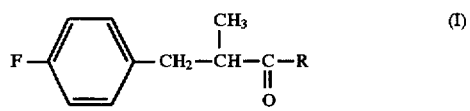

in which R is a hydroxy group, a linear or branched ($C_1$–$C_8$)-alkoxy group, an aryloxygroup, an amino group or a ($C_1$–$C_8$)-alkylamino group or a ($C_1$–$C_8$)-dialkylamino group, by a) converting p-fluoroaniline into the p-fluorophenyldiazonium salt of the formula (II)

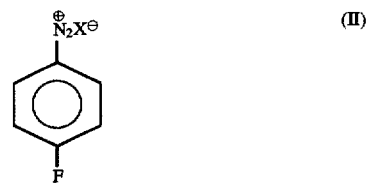

in which X is the equivalent of an anion of an organic or inorganic acid having a pKa value of less than 7, b) reacting the diazonium salt of the formula (II) with a methacrylic acid derivative of the formula (III)

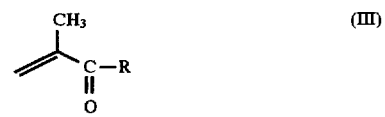

in which R is as defined above in the presence of a palladium catalyst, if desired in the presence of a base and/or a solvent, to give the compounds of the formulae (IV) and (V) in which R is as defined above.

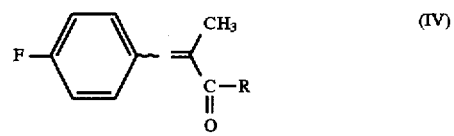

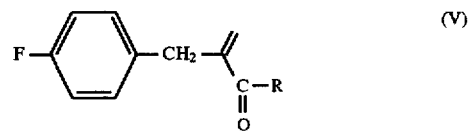

and c) hydrogenating the resulting compounds of the formulae (IV) and (V) in the presence of a palladium catalyst with hydrogen.

15 Claims, No Drawings

PROCESS FOR PREPARING 2-(P-FLUOROPHENYL)-2 METHYL-PROPIONIC ACID AND 3-(P-FLUOROPHENYL)-2-METHYLPROPIONIC ACID DERIVATIVES

This application is a continuation of Ser. No. 08/324,744 filed Oct. 18, 1994 now abandoned.

The present invention relates to a novel process for preparing 3-(p-fluorophenyl)-2-methylpropionic acid and 3-(p-fluorophenyl)-2-methylpropionic acid derivatives.

3-(p-Fluorophenyl)-2-methylpropionic acid and 3-(p-fluorophenyl)-2-methylpropionic acid derivatives are of industrial importance as pharmaceutical intermediates. They are important in particular as intermediates for analgesics, antipyretics and antiphlogistics such as Sulindac.

Previous syntheses of such intermediates start, for example, from the corresponding p-fluorobenzaldehyde which is reacted in the presence of stoichiometric amounts of base with propionic anhydride. Reduction with hydrogen in the presence of palladium on activated carbon as the catalyst then gives β-aryl-2-methylpropionic acid (U.S. Pat. No. 3,654,349).

β-Aryl-2-methylpropionic acid can also be prepared by reacting p-fluorobenzaldehyde with a substituted acetic ester in a Claisen-type reaction or with a halogenated propionic ester in a Reformatsky-type reaction (DE 2,039,426).

The processes described have the following disadvantages:

The p-fluorobenzaldehyde used is a compound which can only be prepared in industry at very high cost (>80 DM/kg). Moreover, preparation of the starting material results in the formation of relatively large amounts of salts which makes the overall synthesis problematical in terms of ecology.

The subsequent reaction of p-fluorobenzaldehyde with propionic anhydride or with a halogenated propionic ester again produces large amounts of salt. The patents mentioned give no details regarding the yield of the reaction of p-fluorobenzaldehyde with propionic anhydride. Based on analogous examples such as the reaction of 2,4-difluorobenzaldehyde, it must be assumed that the yield is not more than 70 to 80%.

Accordingly, there was a considerable need for a process which produces 3-(p-fluorophenyl)-2-methylpropionic acid and its derivatives in high yield without any troublesome impurities and in a simple manner and which additionally provides a simple industrial reaction.

This object is achieved by a process for preparing 3-(p-fluorophenyl)-2-methylpropionic acid and derivatives thereof of the formula (I),

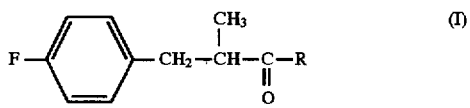

in which R is a hydroxy group, a linear or branched $(C_1-C_8)$-alkoxy group, an aryloxy group, an amino group or a $(C_1-C_8)$-alkylamino group or a $(C_1-C_8)$-dialkylamino group, which process comprises a) converting p-fluoroaniline into the p-fluorophenyldiazonium salt of the formula (II)

in which X is the equivalent of an anion of an organic or inorganic acid having a pKa value of less than 7, b) reacting the diazonium salt of the formula (II) with a methacrylic acid derivative of the formula (III)

in which R is as defined above in the presence of a palladium catalyst, if desired in the presence of a base and/or a solvent, to give the compounds of the formulae (IV) and (V) in which R is as defined above,

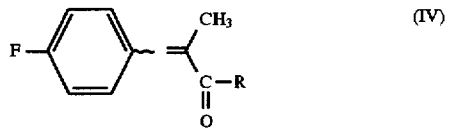

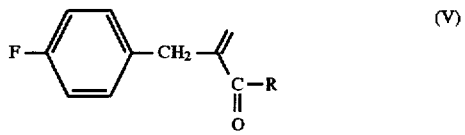

c) hydrogenating the resulting compounds of the formulae (IV) and (V) in the presence of a palladium catalyst using hydrogen.

In a preferred reaction variant, diazotization and olefination of the diazonium salt are carried out in one step, thus making it possible to prepare the desired product in only two steps.

As for the meaning of the radical R, the substituent R can be, for example, a methoxy, ethoxy, n-propyloxy, isopropyloxy, n-butyloxy, i-butyloxy, tert.-butyloxy, n-pentyloxy, i-pentyloxy, n-hexyloxy, n-heptyloxy, n-octyloxy, 2-ethylhexyloxy, 2-ethyldecyloxy, n-decyloxy, n-dodecyloxy, hydroxyl group, furthermore an N,N-dimethylamino, N,N-diethylamino, N-methylamino, N-ethylamino, N,N-methylethylamino, N,N-dipropylamino, N,N-dibutylamino, N-piperidyl, N-morpholino, N-acetamido, N-propionamide group, preferably a hydroxyl, methoxy, ethoxy, n-propyloxy, isopropyloxy, butoxy, N,N-dimethylamino, N,N-diethylamino group, particularly preferably a hydroxyl, methoxy, ethoxy group.

In step b), the palladium catalyst can in principle be used in homogeneous or heterogeneous form. Examples of suitable homogeneous palladium catalysts are palladium(II) acetate, palladium(II) chloride, lithium tetrachloropalladate and palladium(II) bromide. The use of heterogeneous supported palladium catalysts is particularly advantageous. In this case, the palladium catalyst is advantageously applied to a support such as, for example, activated carbon, calcium carbonate, barium sulfate, pumice clay, kieselguhr, silica gel, graphite, magnesium oxide and/or alumina and used in this form. Alternatively, palladium bis(benzylidene)acetone complexes, which are present in some solvents, for example methanol, in heterogeneous form are used. Palladium (benzylidene)acetone complexes are palladium bis (benzylidene)acetone, substituted palladium bis (benzylidene)acetone complexes such as palladium bis(3,3', 4,4'-tetramethoxybenzylidene, acetone complexes, palladium bis(dimethoxybenzylidene/acetone, palladium difluorobis(benzylidene)acetone complexes. Preferably, palladium on activated carbon, palladium(II) acetate or palladium bis(benzylidene) acetone complex are used.

As for the relative ratio of palladium to diazonium salt, it has proved advantageous to use about 0.001 to about 20 mol %, preferably 0.1 to about 1.0 mol %, of palladium, relative to the diazonium salt.

As for the relative ratio of reactants, it is advantageous to react 1 mol of diazonium salt of the formula (III) with about 0.8–20 mol, in particular 1–5 mol, of methacrylic acid derivative.

The procedure of step b) is preferably carried out in protic solvents, such as water, methanol, ethanol or aqueous solutions of alcohols. With certain diazonium salts it may be advantageous to carry out the process in situ, i.e., without isolating the diazonium salts, in an aqueous solution.

A particular advantage of the process according to the invention is that catalyst amounts of less than 1 mol % are sufficient for the olefination of the diazonium salt. Moreover, the addition of bases can be omitted.

The resulting products from step b) are usually present as a mixture of 3-(p-fluorophenyl)methacrylic acid derivatives and 2-(p-fluorobenzyl)acrylic acid derivatives. The isomeric ratio of the two products is in this case usually between 4:1 and 1:1. However, under specific conditions, it is possible to change the isomeric ratio. Since the double bond of the resulting 3-(p-fluorophenyl)methacrylic acid derivatives and 2-(p-fluorobenzyl)acrylic acid derivatives is hydrogenated over the course of the further synthesis, the isomeric ratio is not critical.

Hydrogenation using palladium catalysts leads to 3-(p-fluorophenyl)-2-methylpropionic acid derivatives in high yields.

Owing to the catalytic reaction procedure and the relatively cheap starting material (4-fluoroaniline costs 22 DM/kg; 4-fluorobenzaldehyde costs 80 DM/kg), the novel process is clearly superior to the old processes in terms of economy and ecology. Moreover, the overall yield of the process is 80 to 85%, which is superior to that of the previously described processes.

The examples which follow serve to illustrate the process according to the invention without limiting it thereto.

EXAMPLE 1

71.5 g of 4-fluoroaniline are dissolved in 246.6 g of 50% tetrafluoroboric acid, and the resulting mixture is stirred at 0° to 5° C. for 10 minutes. 47.9 g of sodium nitrite in 55 ml of water are then added at 0° to 5° C. over a period of 20 minutes. The precipitated product is washed with cold ether.

Yield: 96% of 4-fluorophenyldiazonium tetrafluoroborate.

EXAMPLE 2

60.0 g of 4-fluorophenyldiazonium tetrafluoroborate are added at 50° C. to a solution of 57.5 g of methyl methacrylate and 1.65 g (1 mol %) of palladium bis(benzylidene) acetone complex in 200 ml of methanol. The addition took place in portions. The mixture is then stirred at 60° C. for one hour. To isolate the product, the catalyst is filtered off, the reaction mixture is concentrated in vacuo and, after diluting it with dichloromethane, it is washed with water. The crude product is distilled in vacuo to give 49.9 g of a 1.6:1 mixture of methyl 3-(p-fluorophenyl)methacrylate and methyl 2-(p-fluorobenzyl)acrylate.

Yield: 90% of methyl 3-(p-fluorophenyl)methacrylate and methyl 2-(p-fluorobenzyl)acrylate. $^1$H-NMR for methyl 3-(p-fluorophenyl)methacrylate: 2.04 (d, J=1.5 Hz, 3H, CH$_3$), 3.80 (s, 3H, CO$_2$CH$_3$), 6.82–7.40 (m, 4H, phenyl-H), 7.62 (s, br., 1H, vinyl-H). $^1$H-NMR for methyl 2-(p-fluorobenzyl)acrylate: 3.55 (s, br., 2H, benzyl-H), 3.74 (s, 3H, CO$_2$CH$_3$), 5.47, 6.23 (2m, 2H, =CH$_2$), 6.83–7.38 (m, 4H, phenyl-H).

EXAMPLE 3

10.0 g of 4-fluorophenyldiazonium tetrafluoroborate are added at 50° C. to a solution of 19.3 g of methyl methacrylate and 69 mg (0.25 mol %) of palladium bis(benzylidene) acetone complex in 50 ml of methanol. The addition took place in portions and after half has been added 69 mg (0.25 mol %) of the palladium catalyst are again added. The mixture is then stirred at 60° C. for one hour. To isolate the product, the catalyst is filtered off, the reaction mixture is concentrated in vacuo and, after diluting it with dichloromethane, it is washed with water. The crude product is chromatographed to give 7.99 g of a 1.5:1 mixture of methyl 3-(p-fluorophenyl)methacrylate and methyl 2-(p-fluorobenzyl)acrylate.

Yield: 87% of methyl 3-(p-fluorophenyl)methacrylate and methyl 2-(p-fluorobenzyl)acrylate.

EXAMPLE 4

10.0 g of 4-fluorophenyldiazonium tetrafluoroborate are added at 0° C. to a solution of 19.3 g of methyl methacrylate in 50 ml of methanol. The reaction mixture is heated to 50° C., and 138 mg (0.25 mol %) of palladium bis(benzylidene) acetone complex are added in portions. The mixture is then stirred at 60° C. for one hour. To isolate the product, the catalyst is filtered off, the reaction mixture is concentrated in vacuo and, after diluting it with dichloromethane, it is washed with water. The crude product is chromatographed to give 7.00 g of a 1.5:1 mixture of methyl 3-(p-fluorophenyl)methacrylate and methyl 2-(p-fluorobenzyl) acrylate.

Yield: 75% of methyl 3-(p-fluorophenyl)methacrylate and methyl 2-(p-fluorobenzyl)acrylate.

EXAMPLE 5

60.0 g of 4-fluorophenyldiazonium tetrafluoroborate are added at 50° C. to a solution of 57.5 g of methyl methacrylate and 330 mg (0.2 mol %) of palladium bis(benzylidene) acetone complex in 200 ml of methanol. The addition took place in portions and after half has been added 165 mg (0.1 mol %) of palladium catalyst are again added. The mixture is then stirred at 60° C. for one hour. To isolate the product, the catalyst is filtered off, and the reaction mixture is distilled in vacuo to give 48.8 g of a 1.6:1 mixture of methyl 3-(p-fluorophenyl)methacrylate and methyl 2-(p-fluorobenzyl)acrylate.

Yield: 88% of methyl 3-(p-fluorophenyl)methacrylate and methyl 2-(p-fluorobenzyl)acrylate.

EXAMPLE 6

10.0 g of 4-fluorophenyldiazonium tetrafluoroborate are added at 50° C. to a solution of 19.3 g of methyl methacrylate and 0.25 mol % of palladium bis(3,3', 4,4'-tetramethoxybenzylidene)acetone complex in 50 ml of methanol. The addition took place in portions and after half has been added 0.1 mol % of palladium catalyst is again added. The mixture is then stirred at 60° C. for one hour. To isolate the product, the catalyst is filtered off, the reaction mixture is concentrated in vacuo and, after diluting it with dichloromethane, it is washed with water. The crude product is chromatographed to give 8.54 g of a 1.7:1 mixture of methyl 3-(p-fluorophenyl)methacrylate and methyl 2-(p-fluorobenzyl)acrylate.

Yield: 93% of methyl 3-(p-fluorophenyl)methacrylate and methyl 2-(p-fluorobenzyl)acrylate.

EXAMPLE 7

10.0 g of 4-fluorophenyldiazonium tetrafluoroborate are added at 50° C. to a solution of 19.3 g of methyl methacrylate and 69 mg (0.25 mol %) of palladium bis(benzylidene) acetone complex in 50 ml of ethanol. The addition took place in portions and after half has been added 69 mg (0.25 mol %) of the palladium catalyst are again added. The mixture is then stirred at 60° C. for one hour. To isolate the product, the catalyst is filtered off, the reaction mixture is concentrated in vacuo and, after diluting it with dichloromethane, it is washed with water. The crude product is chromatographed.

Yield: 84% of methyl 3-(p-fluorophenyl)methacrylate and methyl 2-(p-fluorobenzyl)acrylate.

EXAMPLE 8

50 g of 4-fluoroaniline are dissolved in 173 g of 50% tetrafluoroboric acid and the resulting mixture is stirred at 0° to 5° C. for 10 minutes. 33.5 g of sodium nitrite in 40 ml of water are then added at 0° to 5° C. over a period of 20 minutes. 0.5 g of urea, 100 ml of methanol, 2.58 g of palladium bis(benzylidene)acetone complex and 180 g of methyl methacrylate are then added to the mixture. The reaction mixture is heated to 60°–70° C. and stirred at this temperature until evolution of nitrogen is complete.

The phases are then separated, and the aqueous phase is extracted with ethyl acetate. The combined organic phases are distilled.

Yield: 82% of methyl 3-(p-fluorophenyl)methacrylate and methyl 2-(p-fluorobenzyl)acrylate.

EXAMPLE 9

A mixture of 10.0 g of methyl 3-(p-fluorophenyl) methacrylate and methyl 2-(p-fluorobenzyl)acrylate are stirred together with 0.5 g of 5% palladium on activated carbon in 30 ml of methanol in an autoclave at 50° C. for 3 hours. After cooling and filtering off the catalyst, the product is purified by chromatography.

Yield: 92% of methyl 3-(4-fluorophenyl)propionate.

What is claimed is:

1. A process for preparing 3-(p-fluorophenyl)-2-methylpropionic acid and derivatives thereof of the formula (I),

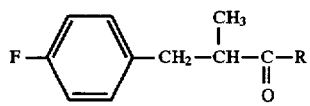

in which R is a hydroxy group, a linear or branched ($C_1$–$C_8$)-alkoxy group, an aryloxy group, an amino group or a ($C_1$–$C_8$)-alkylamino group or a ($C_1$–$C_8$)-dialkylamino group, which process consists essentially of a) converting p-fluoroaniline into a p-fluorophenyldiazonium salt of the formula (II)

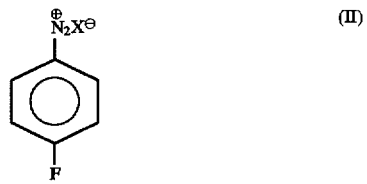

in which X is the equivalent of an anion of an organic or inorganic acid having a pKa value of less than 7, b) reacting the diazonium salt of the formula (II) with a methacrylic acid derivative of the formula (III)

in which R is as defined above in the presence of a palladium catalyst, if desired in the presence of a base and/or a solvent, to give the compounds of the formulae (IV) and (V) in which R is as defined above,

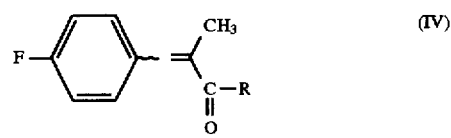

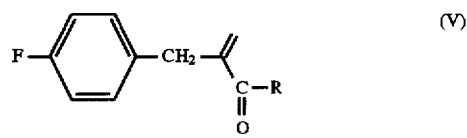

and c) hydrogenating the resulting compounds of the formulae (IV) and (V) in the presence of a palladium catalyst with hydrogen.

2. The process as claimed in claim 1, wherein step a) and step b) are carried out as a one-pot reaction.

3. The process as claimed in claim 1, wherein the reaction with the methacrylic acid derivative of the formula (III) is carried out at temperatures of 0° to 120° C.

4. The process as claimed in claim 3, and the reaction with the methacrylic acid derivative of the formula (III) is carried out at temperatures of 20° to 100° C.

5. The process as claimed in claim 3, and the reaction with the methacrylic acid derivative of the formula (III) is carried out at temperatures of 30° to 80° C.

6. The process as claimed in claim 1,
 wherein for step b) the palladium catalyst is used in heterogeneous form.

7. The process as claimed in claim 6, wherein the palladium catalyst is applied to a support.

8. The process as claimed in claim 7, wherein the palladium catalyst is applied to an activated carbon support.

9. The process as claimed in claim 7, wherein the palladium catalyst is applied to a support selected from the groups consisting of calcium carbonate, barium sulfate, pumice, clay, kieselguhr, silica gel, graphite, magnesium oxide or alumina.

10. The process as claimed in claim 6, wherein palladium bis(benzylidene)acetone compounds are used in heterogeneous form.

11. The process as claimed in claim 1, wherein the step b) 0.001 to 1 mol % of palladium, relative to the diazonium salt, is used.

12. The process as claimed in claim 1, wherein the step b) 1 mol of diazonium salt is reacted with 0.8 to 20 mol of methacrylic acid derivative.

13. The process as claimed in claim 1,
wherein in step b) the solvent used is water, methanol, ethanol or mixtures thereof.

14. The process as claimed in claim 1, wherein in step b) 0.01 to 0.8 mol % of palladium, relative to the diazonium salt, is employed.

15. The process as claimed in claim 1, wherein in step b) 1 mol of diazonium salt is reacted with 1 to 5 mol of methacrylic acid derivative.

* * * * *